(12) United States Patent
Mohseni et al.

(10) Patent No.: US 12,161,479 B2
(45) Date of Patent: Dec. 10, 2024

(54) METHOD AND SYSTEM FOR MULTISPECTRAL IMAGING

(71) Applicant: Northwestern University, Evanston, IL (US)

(72) Inventors: Hooman Mohseni, Wilmette, IL (US); Iman Hassani Nia, Evanston, IL (US); Skyler Wheaton, Evanston, IL (US)

(73) Assignee: Northwestern University, Evanston, IL (US)

( * ) Notice: Subject to any disclaimer, the term of this patent is extended or adjusted under 35 U.S.C. 154(b) by 911 days.

(21) Appl. No.: 17/047,465

(22) PCT Filed: Apr. 23, 2019

(86) PCT No.: PCT/US2019/028692
§ 371 (c)(1),
(2) Date: Oct. 14, 2020

(87) PCT Pub. No.: WO2019/226261
PCT Pub. Date: Nov. 28, 2019

(65) Prior Publication Data
US 2021/0113148 A1 Apr. 22, 2021

Related U.S. Application Data

(60) Provisional application No. 62/661,875, filed on Apr. 24, 2018.

(51) Int. Cl.
*H04N 23/11* (2023.01)
*A61B 5/00* (2006.01)
(Continued)

(52) U.S. Cl.
CPC ............ *A61B 5/444* (2013.01); *A61B 5/0075* (2013.01); *G01J 3/0208* (2013.01); *G01J 3/108* (2013.01);
(Continued)

(58) Field of Classification Search
CPC ...... A61B 5/444; A61B 5/0075; H04N 23/11; G01J 3/0208; G01J 3/108; G01J 3/2823
See application file for complete search history.

(56) References Cited

U.S. PATENT DOCUMENTS

2005/0134180 A1\* 6/2005 Ikeuchi ................. H01J 61/822
  313/574
2008/0158679 A1 7/2008 Luty et al.
(Continued)

FOREIGN PATENT DOCUMENTS

WO  WO 2010/022391 A2  2/2010

OTHER PUBLICATIONS

The International Search Report and Written Opinion issued for International Patent Application No. PCT/US19/28692 on Nov. 14, 2019, pp. 1-9.

*Primary Examiner* — Daniel L Cerioni
(74) *Attorney, Agent, or Firm* — Bell & Manning, LLC

(57) ABSTRACT

A multispectral imaging apparatus includes a processor and a plurality of sets of light-emitting diodes (LEDs) in communication with the processor. One or more first sets of LEDs has a wavelength in a visible range, and one or more second sets of LEDs has a wavelength in a short wavelength infrared range. The apparatus includes a truncated source cone through which light from the plurality of sets of LEDs is directed onto a surface and through which light reflected off of the surface is received. The apparatus also includes a visible light camera configured to capture a first image of the surface based on reflected light that originates from the one or more first sets of LEDS. The apparatus further includes an infrared light camera and configured to capture a second image of the surface based on reflected light that originates from the one or more second sets of LEDs.

14 Claims, 18 Drawing Sheets

(51) Int. Cl.
*G01J 3/02* (2006.01)
*G01J 3/10* (2006.01)
*G01J 3/28* (2006.01)

(52) U.S. Cl.
CPC ............ *G01J 3/2823* (2013.01); *H04N 23/11* (2023.01); *G01J 2003/104* (2013.01); *G01J 2003/2826* (2013.01)

(56) References Cited

U.S. PATENT DOCUMENTS

| | | |
|---|---|---|
| 2012/0092131 A1 | 4/2012 | Vasic et al. |
| 2014/0078379 A1 | 3/2014 | Masuda et al. |
| 2017/0091550 A1 | 3/2017 | Feng et al. |
| 2017/0124709 A1 | 5/2017 | Rithe et al. |
| 2017/0205344 A1 | 7/2017 | Gemp et al. |

* cited by examiner

THE REFLECTIVE SURFACE TILT

NORMAL INCIDENT TO THE REFLECTIVE SURFACE

METHOD AND SYSTEM FOR MULTISPECTRAL IMAGING

CROSS-REFERENCE TO RELATED APPLICATION

This application is a National Stage of International Application No. PCT/US19/28692, filed Apr. 23, 2019, which claims the benefit of U.S. Patent Application No. 62/661,875, filed Apr. 24, 2018, the contents of which are herein incorporated by reference.

REFERENCE TO GOVERNMENT RIGHTS

This invention was made with government support under Grant No. W911NF-11-1-0390 awarded by the Army Research Office (ARO). The government has certain rights in the invention.

BACKGROUND

Skin cancer refers to a disease in which damaged skin cells multiply uncontrollably to form malignant tumors. In many cases, the skin cells become damaged due to ultraviolet radiation received from the sun or other sources. In other cases, such as melanoma, the skin cancer can develop in areas that are not exposed to the sun or other utraviolet radiation. While there are many different types of skin cancer, the most common types include basal cell carninoma, squamous cell carcinoma, and melanoma. The ability to treat and cure skin cancer often depends on early detection. If not detected early enough or if allowed to spread, skin cancer can be fatal.

SUMMARY

An illustrative multispectral imaging apparatus includes a processor and a plurality of sets of light-emitting diodes (LEDs) in communication with the processor. One or more first sets of LEDs has a wavelength in a visible range, and one or more second sets of LEDs has a wavelength in a short wavelength infrared range (SWIR). The apparatus also includes a truncated source cone through which light from the plurality of sets of LEDs is directed onto a surface and through which light reflected off of the surface is received. The apparatus also includes a visible light camera in communication with the processor and configured to capture a first image of the surface based on reflected light that originates from the one or more first sets of LEDS with the wavelength in the visible range. The apparatus further includes an infrared light camera in communication with the processor and configured to capture a second image of the surface based on reflected light that originates from the one or more second sets of LEDs with the wavelength in the SWIR.

An illustrative method for performing multispectral imaging includes activating, by a processor, a first set of light-emitting diodes (LEDs) of a multispectral imaging apparatus such that light from the first set of LEDs is emitted onto and reflected off of a surface. The first set of LEDs has a wavelength in a visible light range. The method also includes capturing, by a visible light camera in communication with the processor, a plurality of first images of the surface based on the light from the first set of LEDS that is reflected off of the surface. Each of the plurality of first images is captured using a distinct visible light exposure time. The method also includes activating, by the processor, a second set of light-emitting diodes (LEDs) of the multispectral imaging apparatus such that light from the second set of LEDs is emitted onto and reflected off of the surface. The second set of LEDs has a wavelength in an infrared light range. The method further includes capturing, by an infrared light camera in communication with the processor, a plurality of second images of the surface based on the light from the second set of LEDS that is reflected off of the surface. Each of the plurality of second images is captured using a distinct infrared light exposure time.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

One way to detect skin cancer and other tissue defects is through electromagnetic wave imaging. The absorption and scattering of electromagnetic waves by human skin tissue depends strongly on the wavelength of the electromagnetic waves and also the composition of the tissue. For example, an electromagnetic wave of a given wavelength will be absorbed and scattered in different manners for basal cell carcinoma tissue versus benign tissue. Similarly, the electromagnetic wave of the given wavelength will be absorbed and scattered in different manners for melanoma tissue versus benign tissue, for basal cell carcinoma tissue versus melanoma tissue, and so on. The difference in absorption/scattering between a malignant tumor (e.g., basal cell carcinoma or melanoma) and benign tissue is found to be prominent at visible wavelengths such as ~390 nanometers (nm) to ~700 nm and also at a short wavelength infrared range (SWIR) of ~1400 nm to ~3000 nm.

Figure 1B:
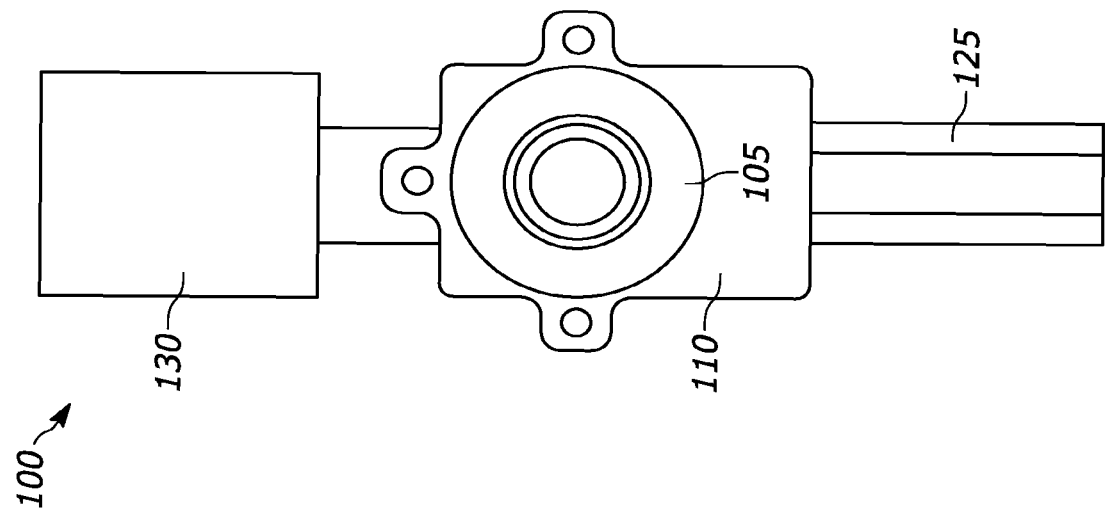
FIG. 1B is a front view of the dermoscope of FIG. 1A in accordance with an illustrative embodiment.
Figure 1A:
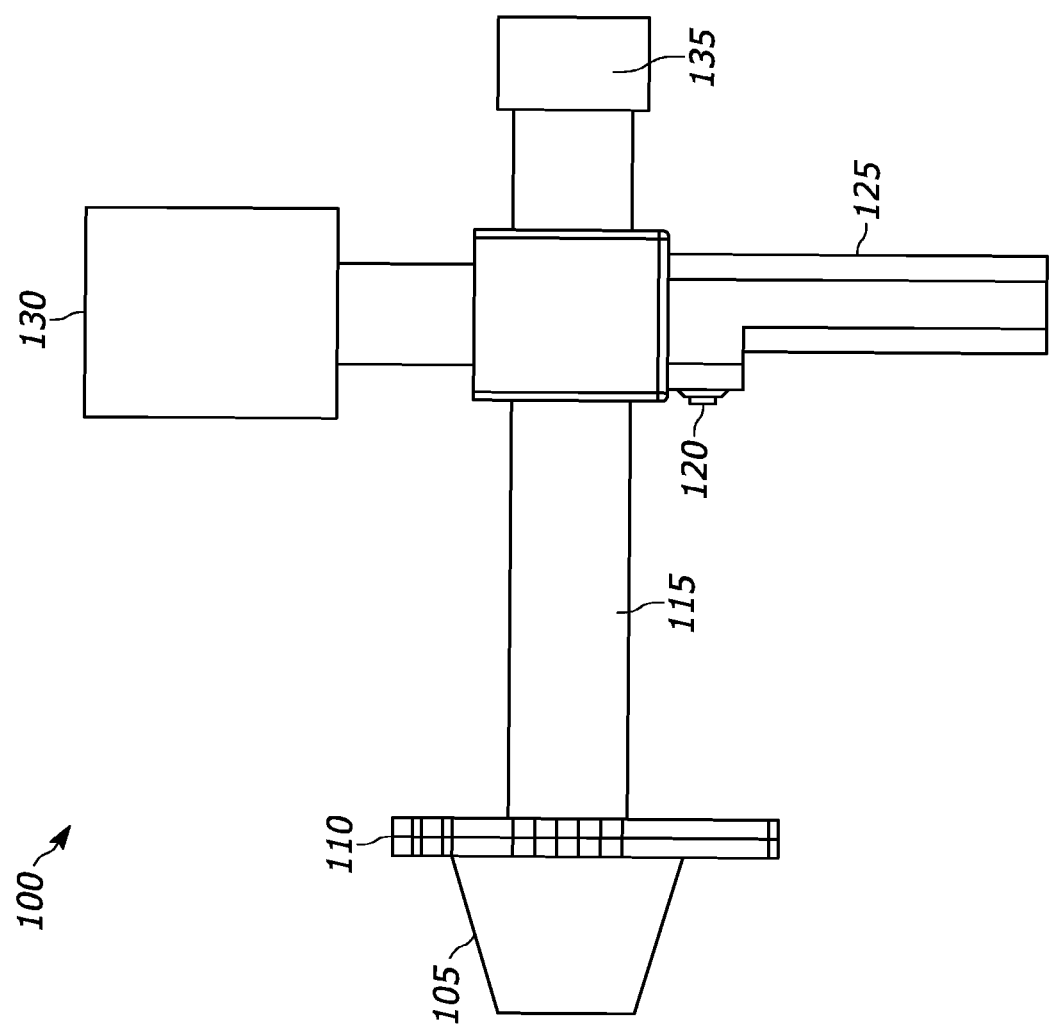
FIG. 1A is a side view of a dermoscope in accordance with an illustrative embodiment.
Figure 1C:
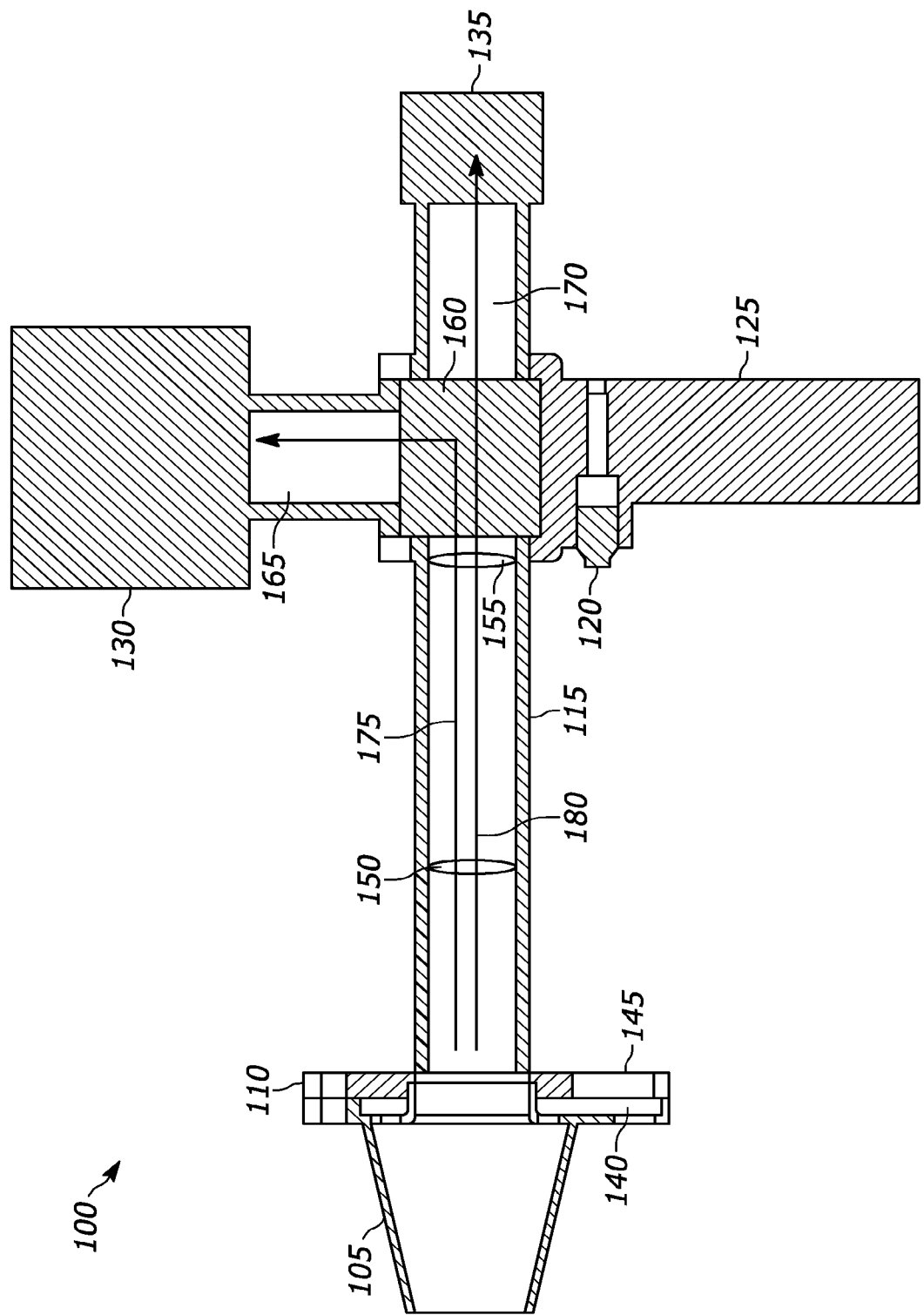
FIG. 1C is a cross-sectional side view of the dermoscope of FIG. 1A in accordance with an illustrative embodiment.

Described herein are systems and methods for high resolution imaging of tissue such as a skin lesion using both visible electromagnetic waves and SWIR electromagnetic waves. The high resolution imaging can be used to extract information such as tissue texture, tissue granularity, tissue asymmetry, and tissue blotchiness such that skin lesions can be identified as benign, melanoma, basal cell carcinoma, etc. FIG. 1A is a side view of a dermoscope 100 in accordance with an illustrative embodiment. FIG. 1B is a front view of the dermoscope 100 in accordance with an illustrative embodiment. FIG. 1C is a cross-sectional side view of the dermoscope 100 in accordance with an illustrative embodiment.

As depicted in FIG. 1A, the dermoscope 100 includes a source cone 105, an electronics case 110, a lens tube 115, a trigger switch 120, a handle 125, an infrared light camera 130, and a visible light camera 135. In alternative embodiments, the dermoscope 100 can include fewer, additional, and/or different components. The source cone 105, which is described in more detail with reference to FIG. 2, is used to direct light from light-emitting diodes (LEDs) onto a surface such as skin tissue. The source cone 105 is also used to direct light reflected off of the skin tissue into the lens tube 115. The trigger switch 120 can be used by an operator to activate the dermoscope 100. The handle 125 can be used by an operator to hold and position the dermoscope 100 for use such that the dermoscope 100 can be a portable unit.

Referring to the cross-sectional view of FIG. 1C, it can be seen that the electronics case 110 of the dermoscope 100 includes a printed circuit board (PCB) 140 and a microcontroller 145. The PCB 140 can include a memory, one or more transceivers, and/or other circuitry as known in the art that allows the dermoscope 100 to function. The memory can be any type of computer memory or storage known in the art, and can include an operating algorithm used to control the dermoscope 100. The one or more transceivers can allow the dermoscope to communicate with other computing devices (e.g., smart phone, laptop computer, server, etc.) via a wired or wireless connection. The computing devices can be used to program the dermoscope, to receive images and image data from the dermoscope, and/or to receive activation/operating instructions from a user.

The PCB 140 can also house or otherwise be in communication with the microcontroller 145 and the LEDs or other light source used for illumination. The microcontroller 145 can be any type of computer processor(s) that can be used to control the dermoscope 100. In one embodiment, the microcontroller 145 can be a Teensy microcontroller. Alternatively, any other type of microcontroller or processor can be used. The electronics case 110 can also house a battery or other power source for the dermoscope 100. In one embodiment, the dermoscope can also include an interface that allows a user to interact with the dermoscope. The interface can include one or more of a display, a key pad, indicator(s), etc.

FIG. 1C also depicts a first lens 150 and a second lens 155 within the lens tube 115. The first lens 150 and the second lens 155 receive light reflected back from a surface (e.g., skin tissue) and help direct the light toward the visible light camera 135 and the infrared light camera 130. In an illustrative embodiment, the first lens 150 and the second lens 155 can provide an optical magnification of one and can have a field of view that is determined by the sensor size of the visible light camera 135 and the infrared light camera 130. In one embodiment, the sensor size for the visible light camera 135 can be 9.2 millimeters (mm) by 5.8 mm and the sensor size for the infrared light camera 130 can be 11.5 mm by 9.2 mm. Alternatively, cameras having different sensor sizes may be used. In one embodiment, the first lens 150 and the second lens 155 can both be 75 mm N-BK7 lenses. In alternative embodiments, a different type of lens may be used or the first lens 150 and the second lens 155 can be different from one another.

A dichroic beam splitter 160 (or dichroic mirror) can be positioned adjacent to or within the lens tube 115. The dichroic splitter 160 is used to direct reflected infrared light into an infrared light tube 165 and toward the infrared light camera 130. The dichroic beam splitter 160 is also used to direct reflected visible light into a visible light tube 170 and toward the visible light camera 135. In FIG. 1C, reflected infrared light is represented by an arrow 175 and reflected visible light is represented by an arrow 180.

Figure 2A:
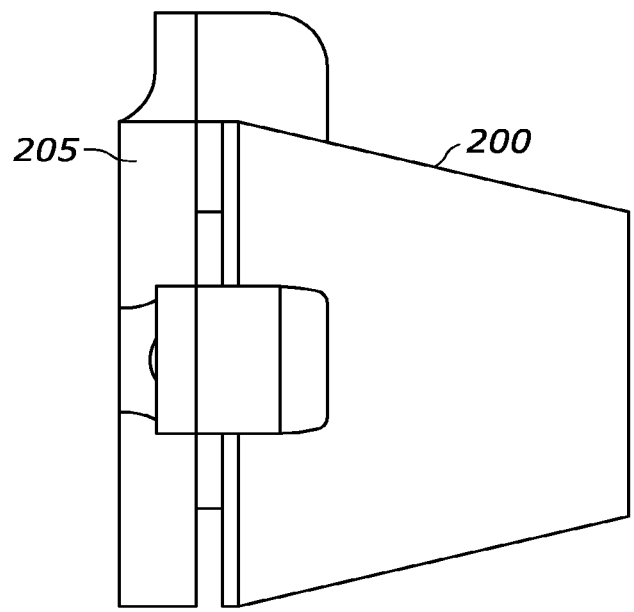
FIG. 2A is a side view of a source cone with an attached electronics case in accordance with an illustrative embodiment.

FIG. 2A is a side view of a source cone 200 with an attached electronics case 205 in accordance with an illustrative embodiment. The source cone 200 is a truncated cone having a base positioned adjacent to the electronics case 205, a sidewall, and a truncated end through which light is emitted onto a surface and received via reflection off of the surface. In one embodiment, the source cone 200 is formed from a polyactic acid (PLA) material using a three-dimensional (3D) printer. In alternative embodiments, any other suitable material and/or process may be used to form the source cone 200.

Figure 2B:
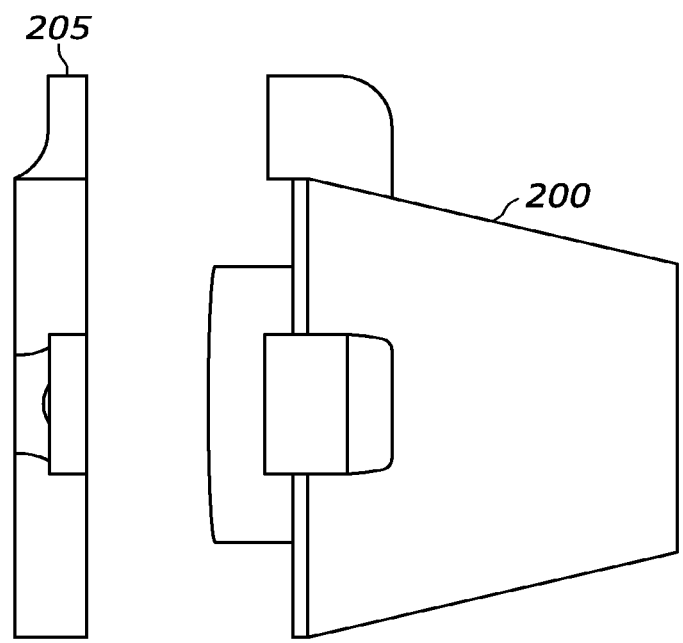
FIG. 2B is a side view of the source cone with the electronics case detached in accordance with an illustrative embodiment.
Figure 2C:
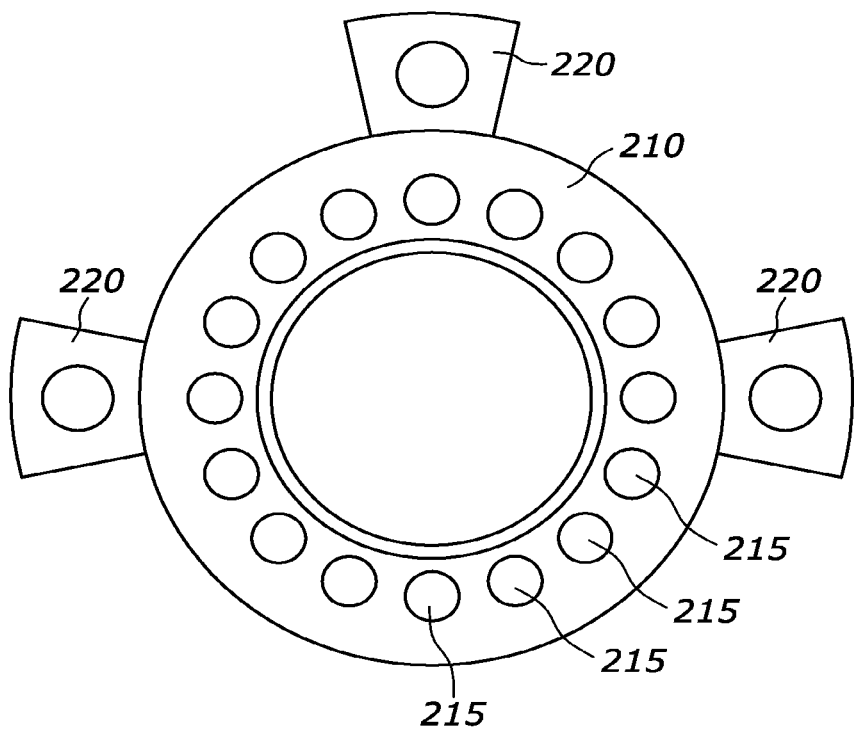
FIG. 2C is a front view of an LED holder in accordance with an illustrative embodiment.
Figure 2D:
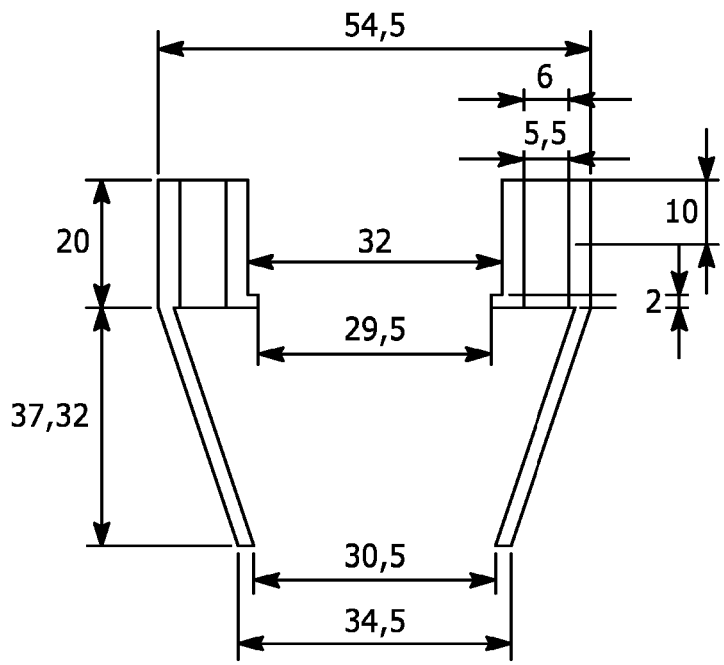
FIG. 2D is a cross-sectional line drawing of a source cone that includes dimensions in accordance with an illustrative embodiment.

FIG. 2B is a side view of the source cone 200 with the electronics case 205 detached in accordance with an illustrative embodiment. FIG. 2C is a front view of an LED holder 210 in accordance with an illustrative embodiment. In an illustrative embodiment, the LED holder 210 can be incorporated into the electronics case 205 such that light can be directed through the source cone 200 and onto a surface such as skin tissue. FIG. 2D is a cross-sectional line drawing of a source cone that includes dimensions (in millimeters) in accordance with an illustrative embodiment. In alternative embodiments, different dimensions may be used for the source cone 200.

As shown in FIG. 2C, the LED holder 210 includes a plurality of openings 215 that are configured to house a corresponding plurality of LEDs. In an illustrative embodiment, the dermoscope can be capable of imaging at 6 different wavelengths such as blue light (~460 nm), green light (~515 nm), red light (~645 nm), SWIR light at 940 nm, SWIR light at 1450 nm, and SWIR light at 1600 nm. In alternative embodiments, the dermoscope may include more or less than 6 different wavelengths. In other alternative embodiments, different visible and/or SWIR wavelengths may also be used.

Figure 3:
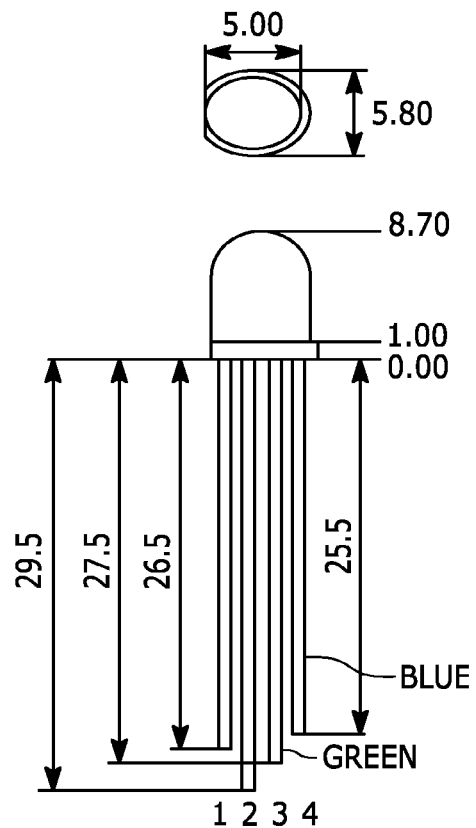
FIG. 3 is a diagram depicting the dimensions and connections for one of the visible light LEDs in accordance with an illustrative embodiment.

As depicted, the LED holder 210 includes 16 openings 215, each of which is configured to house an LED. In an illustrative embodiment, the openings 215 can house 4 SWIR LEDs at 940 nm, 4 SWIR LEDs at 1450 nm, 4 SWIR LEDs at 1450 nm, and 4 visible light LEDs. Each of the 4 visible light LEDs can be capable of producing at least blue light, green light, and red light. FIG. 3 is a diagram depicting example dimensions and connections for one of the visible light LEDs in accordance with an illustrative embodiment. In alternative embodiments, fewer or additional of the openings 215 may be used to incorporate fewer or additional LEDS. For example, alternative embodiments of the system may include more or less than 4 LEDS of a given wavelength, such as 2, 3, 5, 6, etc. Similarly, alternative embodiments of the system may include more or less than 6 different sets of LEDs, such as 2 sets, 4 sets, 8 sets, etc. The LED holder 210 also includes flanges 220 that are used to mount the LED holder 210 to the source cone 200 and/or the electronics case 205.

In an illustrative embodiment, each set of LEDs included in the LED holder 210 is uniformly (symmetrically) positioned around the circle formed by the openings 215. For example, each of the 4 SWIR LEDs at 940 nm can be separated from one another by three other LEDs such that the SWIR LEDs at 940 nm are uniformly arranged within the openings 215. Similarly, each of the 4 visible light LEDs can be separated from one another by other LEDs, and so on. In an alternative embodiment, one or more of the sets of LEDs may not be uniformly arranged within the openings 215.

Figure 4:
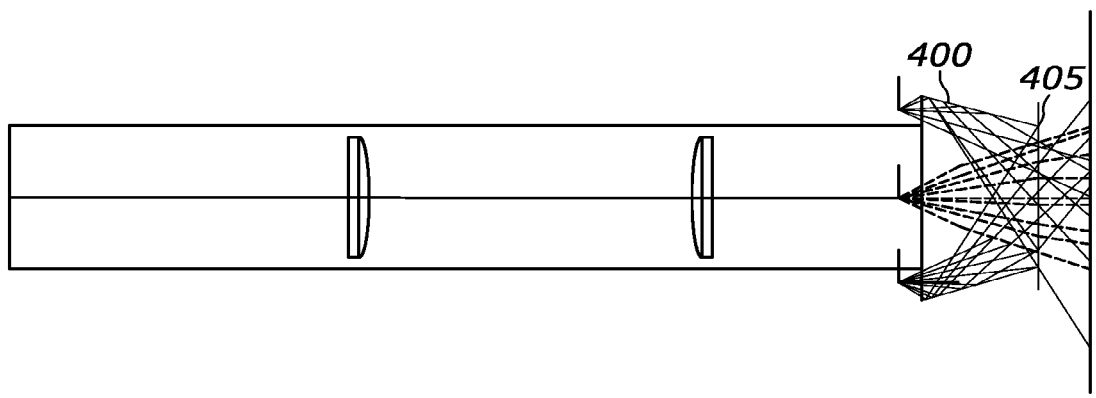
FIG. 4 is a partial cross-sectional side view of the ray tracing simulation in accordance with an illustrative embodiment.

In another illustrative embodiment, an angle of the source cone 200 is 80 degrees (i.e., the angle formed between the base of the cone and the sidewall of the cone). The 80 degree angle of the source cone 200 was determined as optimal using ray tracing simulation software. The simulation modeled each set (or wavelength) of LED light sources as 4 point sources positioned around a periphery of a truncated source cone, and the truncated source cone was modeled as being in contact with a diffusive slice mimicking the optical properties of skin. FIG. 4 is a partial cross-sectional side view of the ray tracing simulation in accordance with an illustrative embodiment. As shown in FIG. 4, rays of light emitted from the LEDs pass through a truncated source cone 400 and contact a diffusive slice 405 that is configured to mimic the optical properties of skin.

To optimize the cone angle, the illumination power of the LED light sources was maximized. The cone angle was then optimized such that the optical power reaching the appropriate camera is maximized when a thin diffusive slice mimicking skin tissue is positioned at the outlet of the truncated source cone. The cone angle was also optimized such that the optical power (or specular reflection) reaching the appropriate camera is minimized when a mirror is positioned at the outlet of the truncated source cone.

Figure 5A:
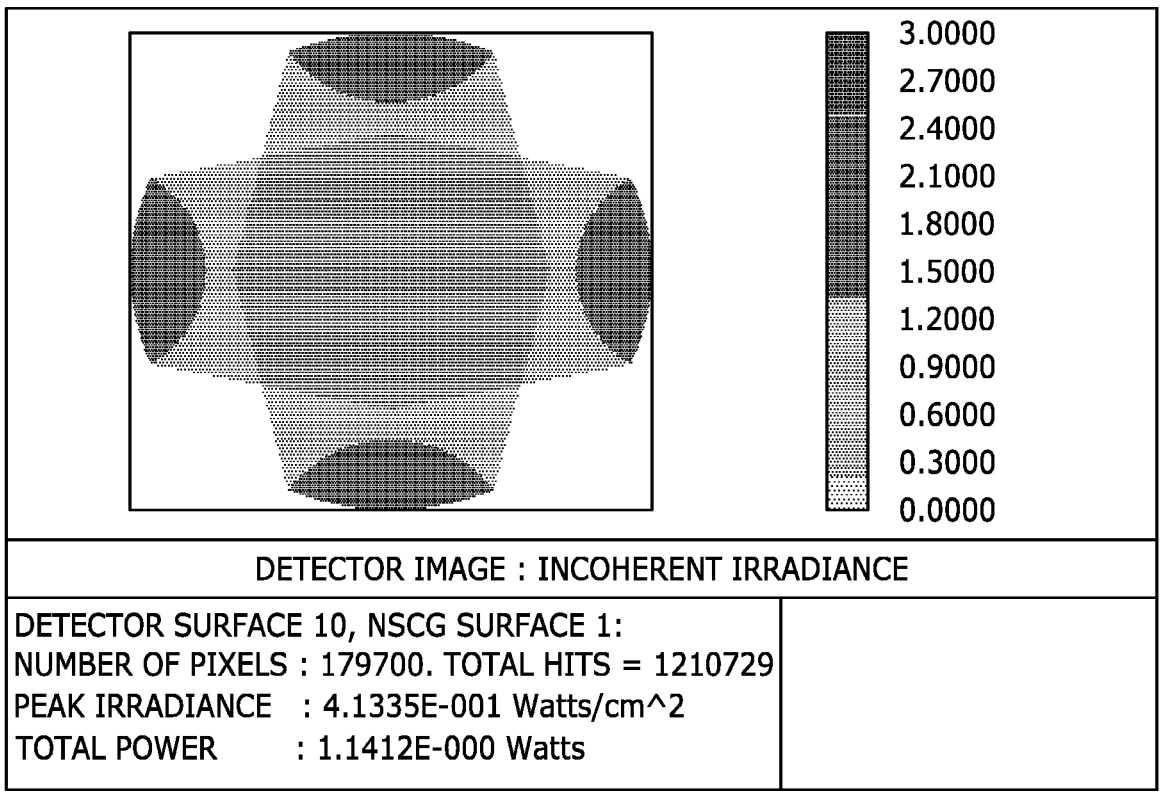
FIG. 5A depicts an optical illumination pattern and power on a sample using a source cone angle of 50° in accordance with an illustrative embodiment.
Figure 5B:
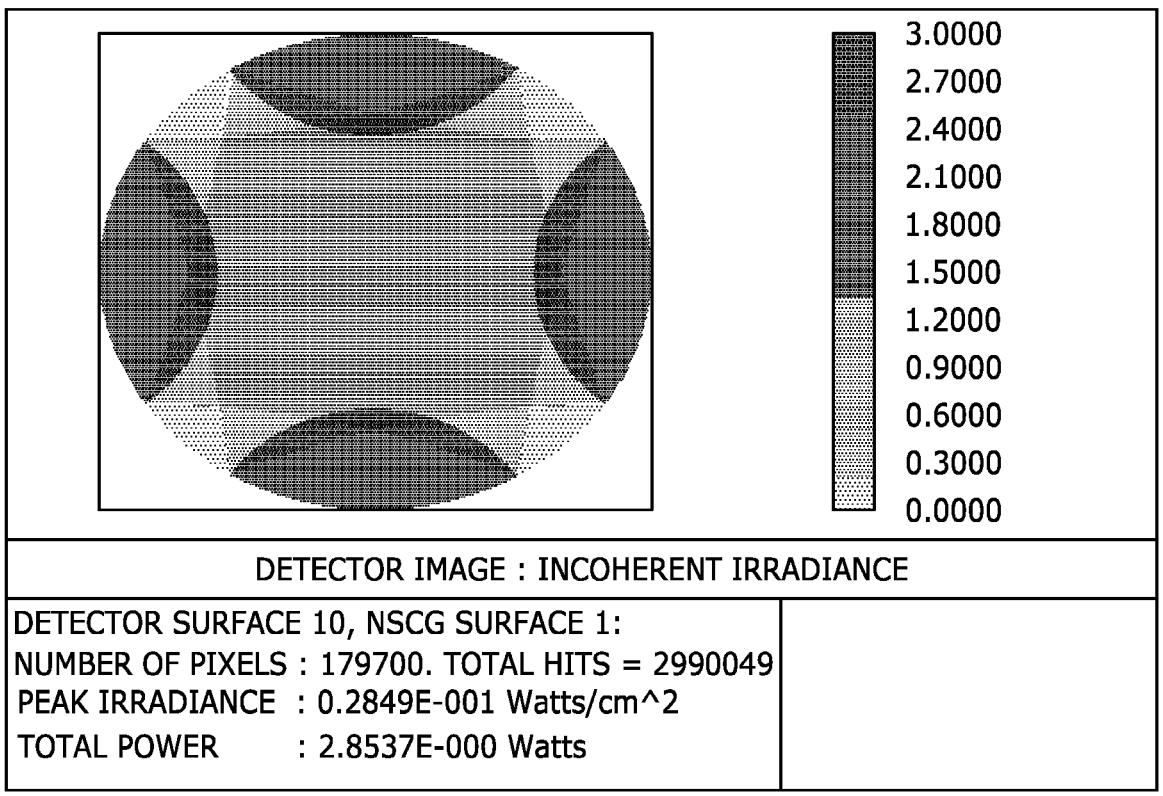
FIG. 5B depicts an optical illumination pattern and power on a sample using a source cone angle of 60° in accordance with an illustrative embodiment.
Figure 5C:
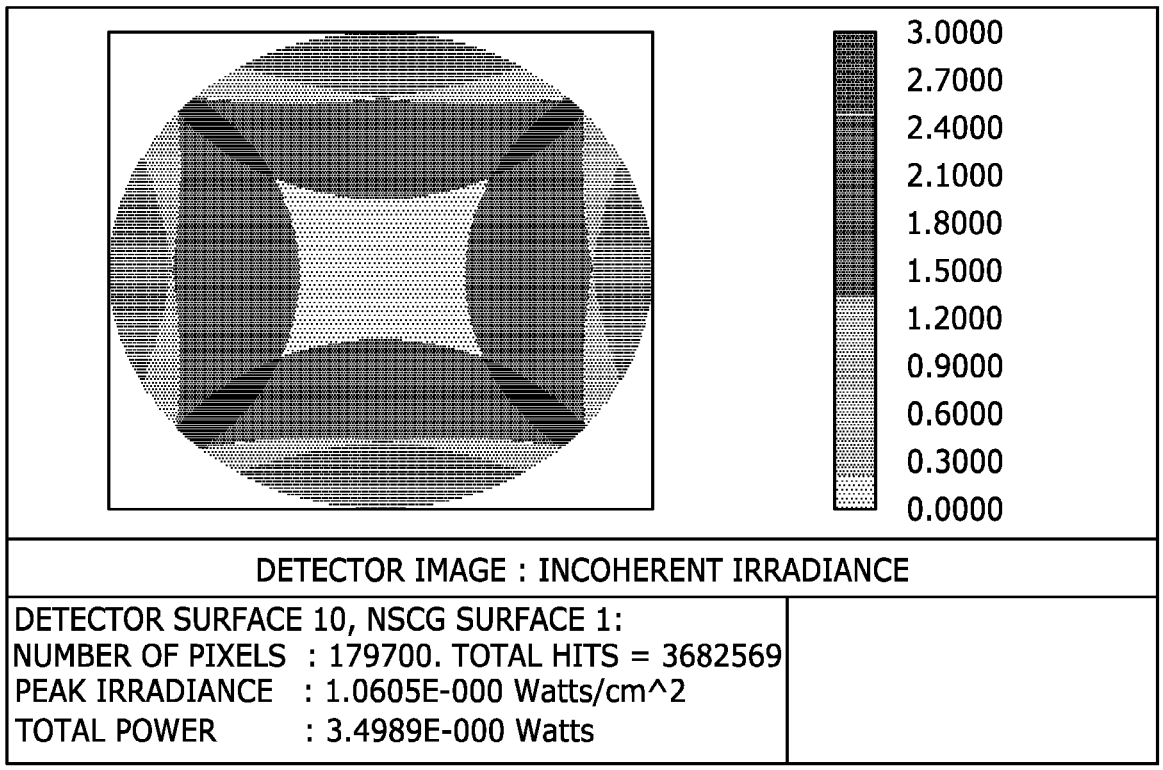
FIG. 5C depicts an optical illumination pattern and power on a sample using a source cone angle of 70° in accordance with an illustrative embodiment.
Figure 5D:
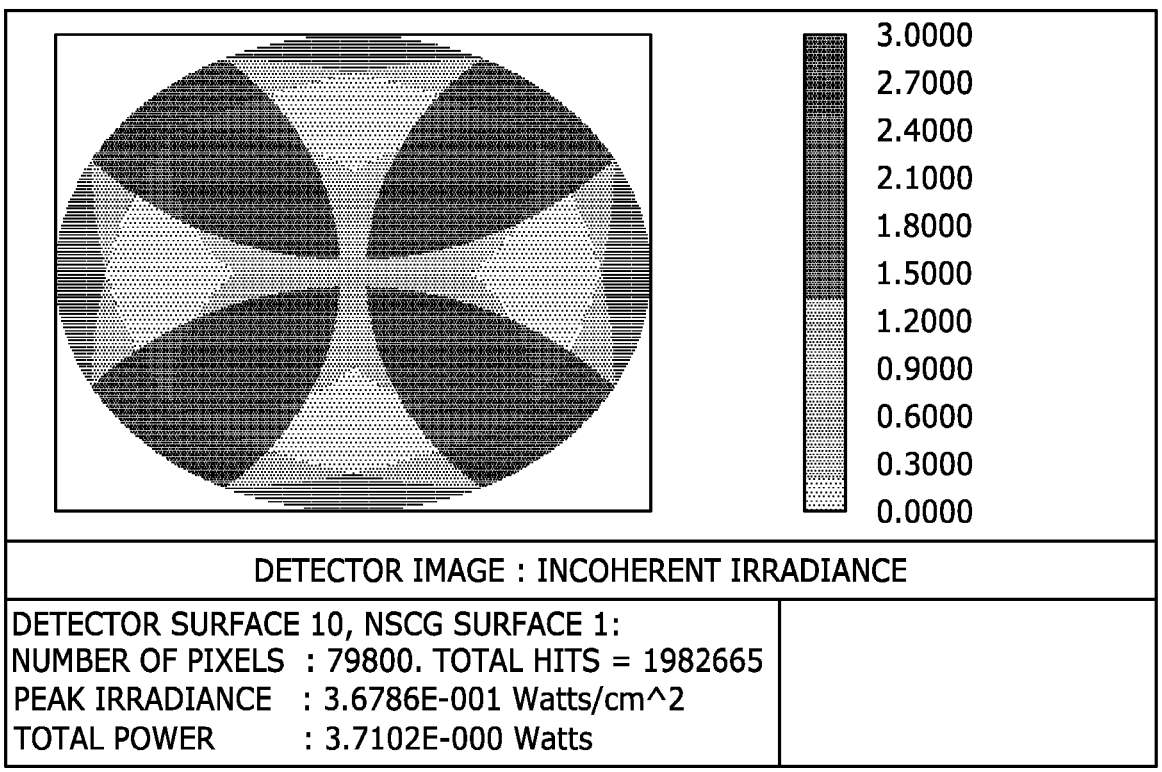
FIG. 5D depicts an optical illumination pattern and power on a sample using a source cone angle of 75° in accordance with an illustrative embodiment.
Figure 5E:
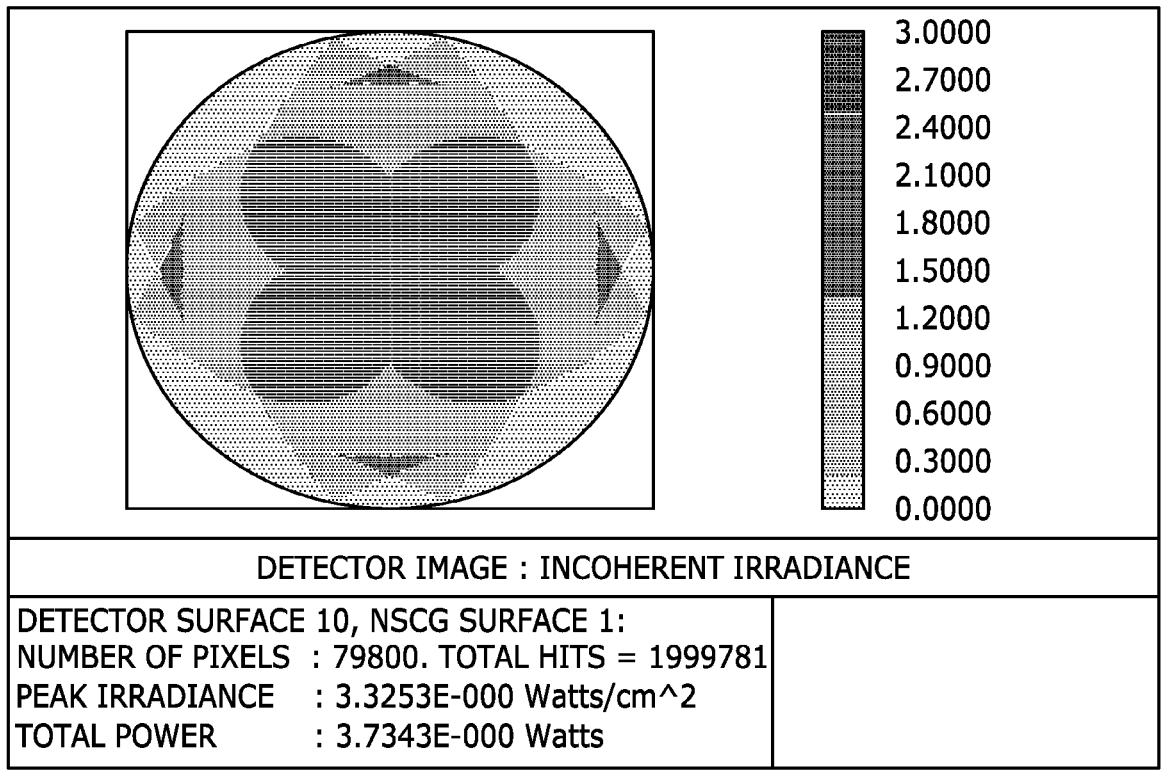
FIG. 5E depicts an optical illumination pattern and power on a sample using a source cone angle of 80° in accordance with an illustrative embodiment.
Figure 5F:
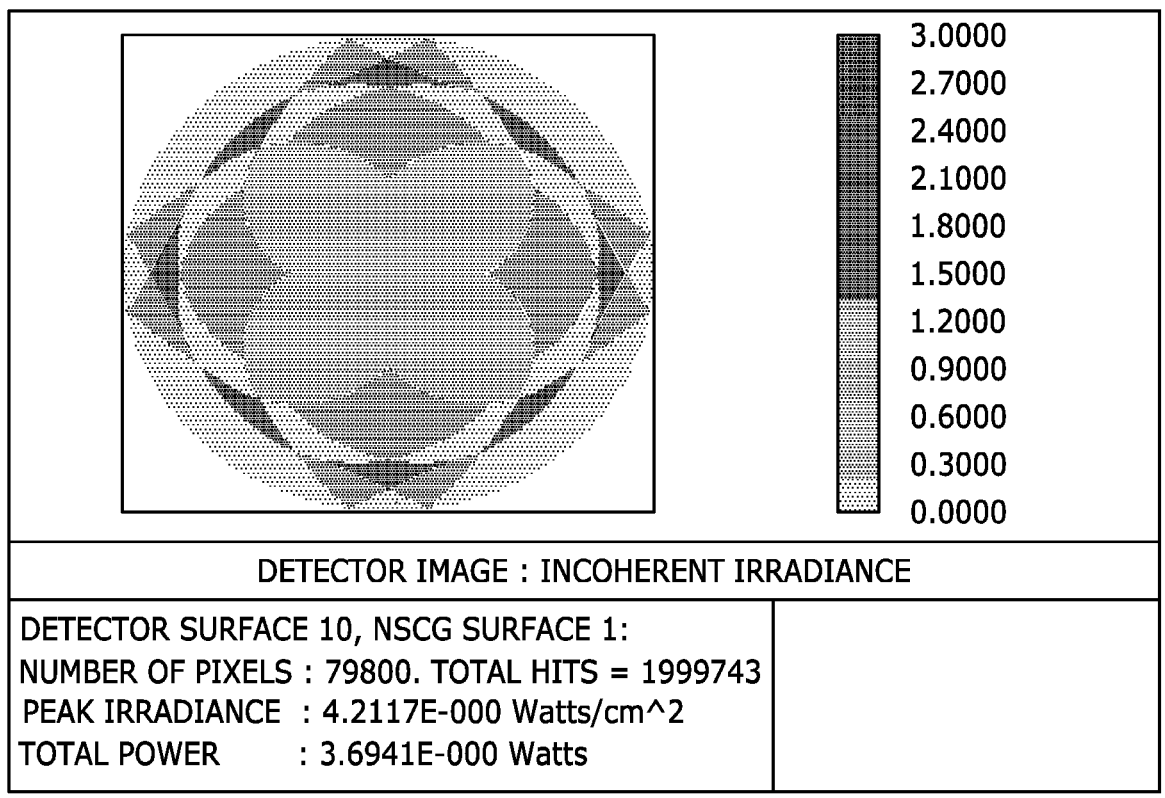
FIG. 5F depicts an optical illumination pattern and power on a sample using a source cone angle of 82° in accordance with an illustrative embodiment.

As discussed above, it was determined that the optimal angle for one configuration of the proposed imaging system is 80 degrees. FIGS. 5A-5F depict an optical illumination pattern and power on a sample for various source cone angles. Specifically, FIG. 5A depicts an optical illumination pattern and power on a sample using a source cone angle of 50° in accordance with an illustrative embodiment. FIG. 5B depicts an optical illumination pattern and power on a sample using a source cone angle of 60° in accordance with an illustrative embodiment. FIG. 5C depicts an optical illumination pattern and power on a sample using a source cone angle of 70° in accordance with an illustrative embodiment. FIG. 5D depicts an optical illumination pattern and power on a sample using a source cone angle of 75° in accordance with an illustrative embodiment. FIG. 5E depicts an optical illumination pattern and power on a sample using a source cone angle of 80° in accordance with an illustrative embodiment. FIG. 5F depicts an optical illumination pattern and power on a sample using a source cone angle of 82° in accordance with an illustrative embodiment. With respect to the results using an 80° source cone angle in FIG. 5E, it can be seen that the illumination pattern is centered and uniform, and that the peak irradiance and total power are maximized as compared to the other source cone angles.

Figure 6A:
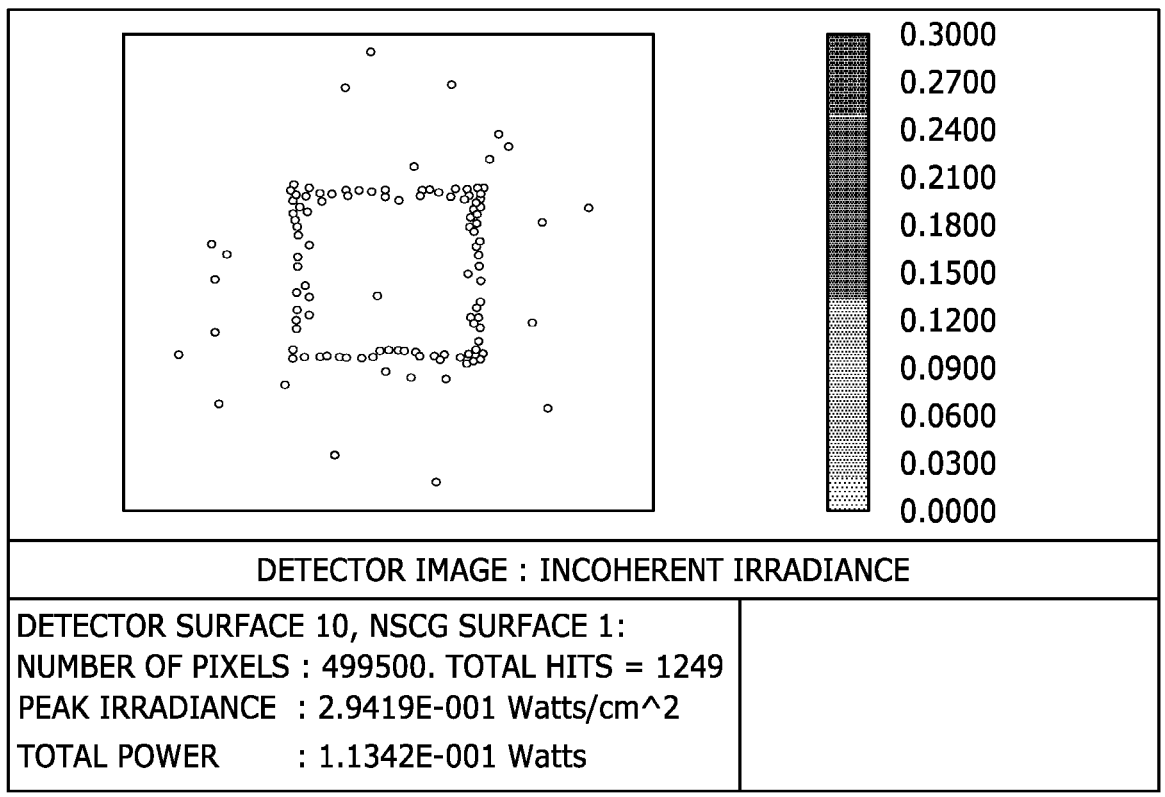
FIG. 6A depicts an optical profile and power reaching the camera using a 50° source cone angle in accordance with an illustrative embodiment.
Figure 6B:
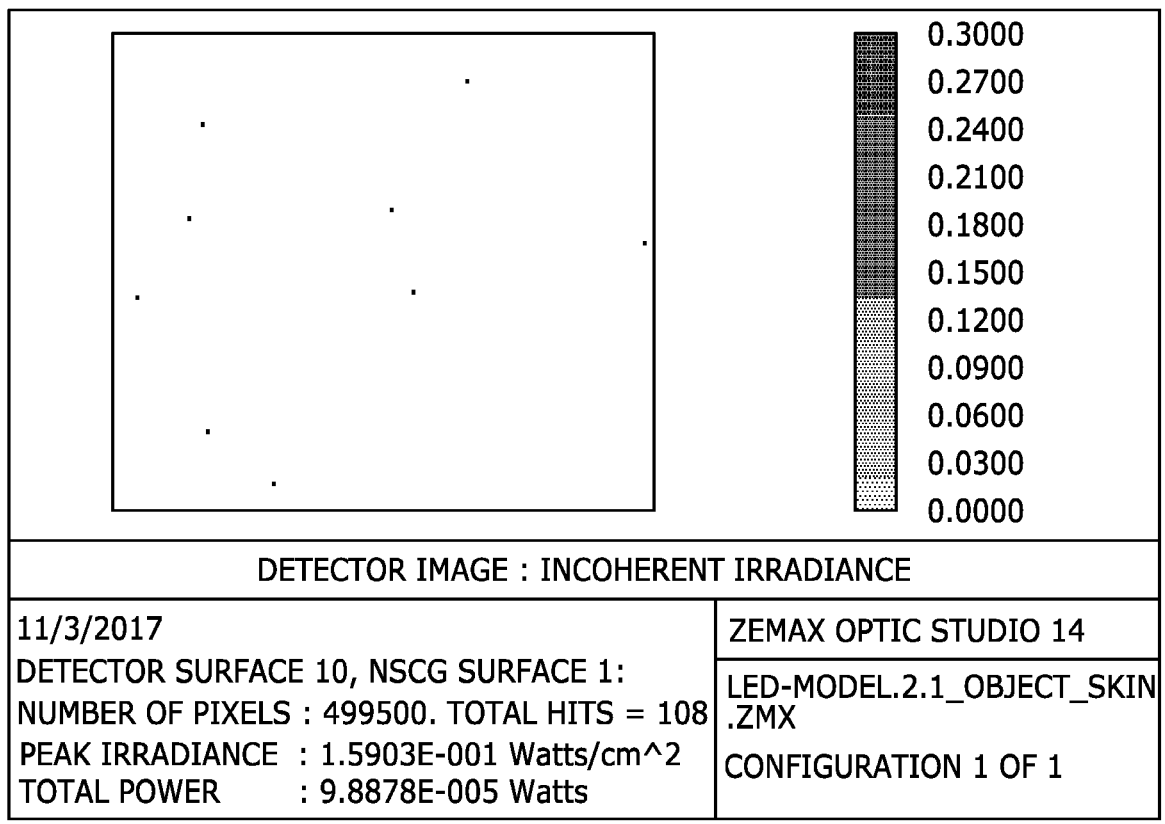
FIG. 6B depicts an optical profile and power reaching the camera using a 60° source cone angle in accordance with an illustrative embodiment.
Figure 6C:
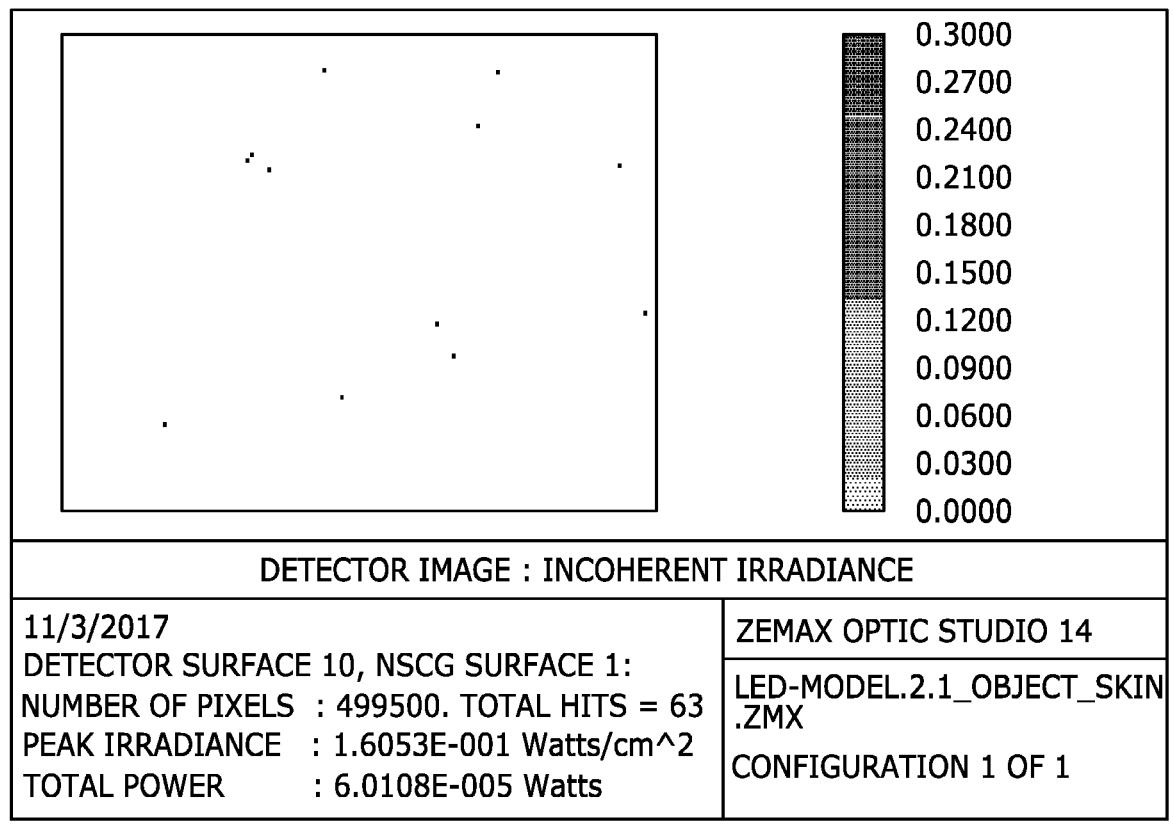
FIG. 6C depicts an optical profile and power reaching the camera using a 70° source cone angle in accordance with an illustrative embodiment.
Figure 6D:
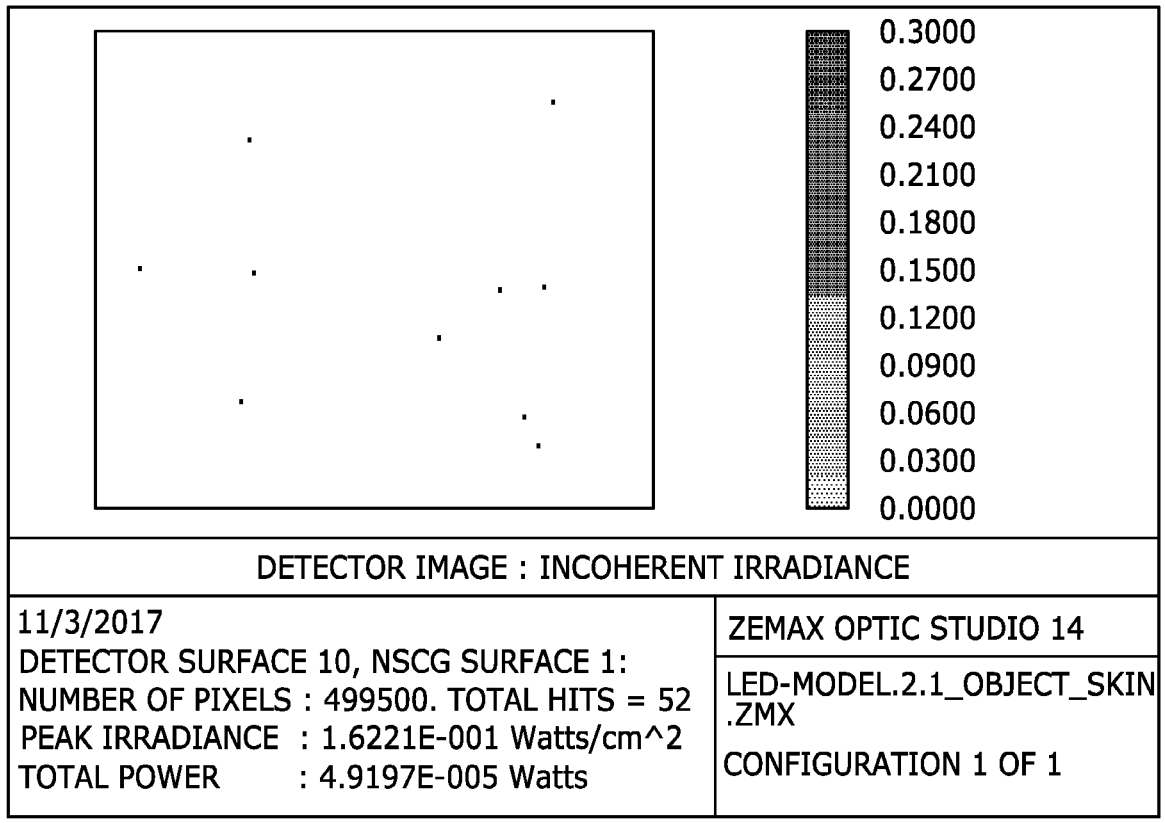
FIG. 6D depicts an optical profile and power reaching the camera using a 75° source cone angle in accordance with an illustrative embodiment.
Figure 6E:
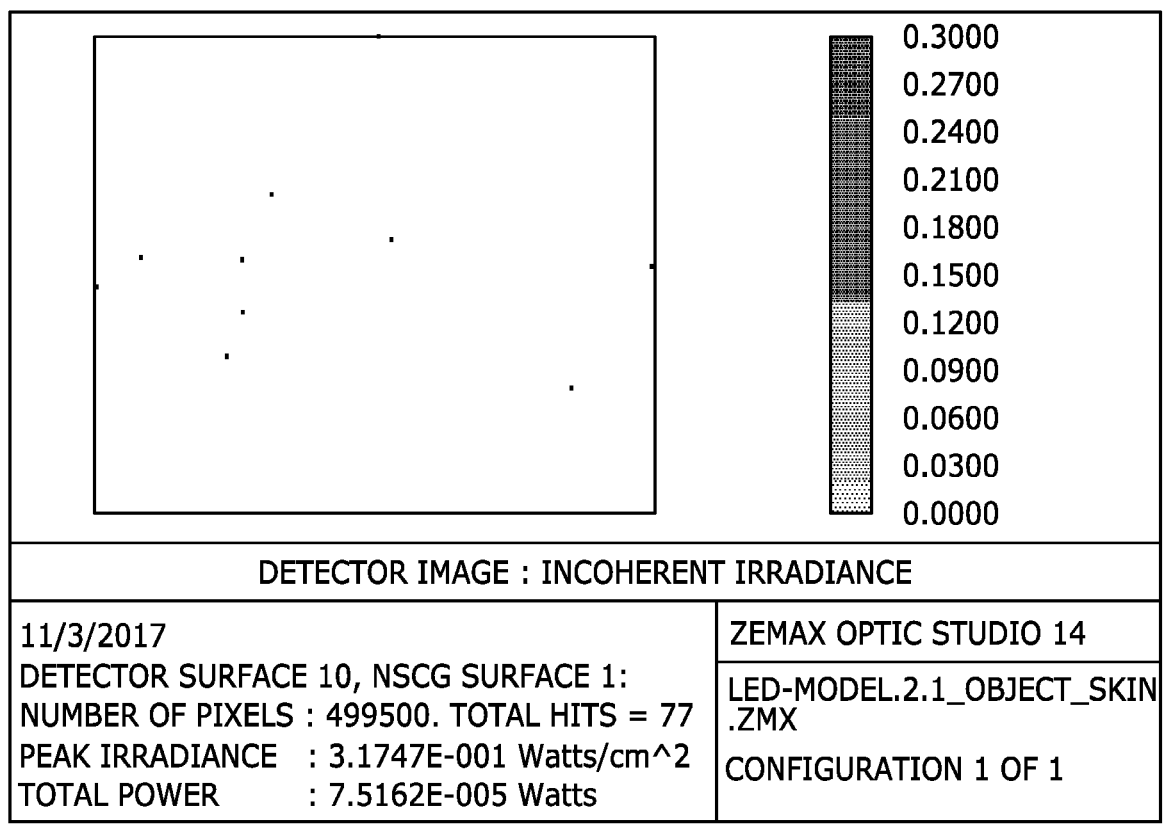
FIG. 6E depicts an optical profile and power reaching the camera using a 80° source cone angle in accordance with an illustrative embodiment.
Figure 6F:
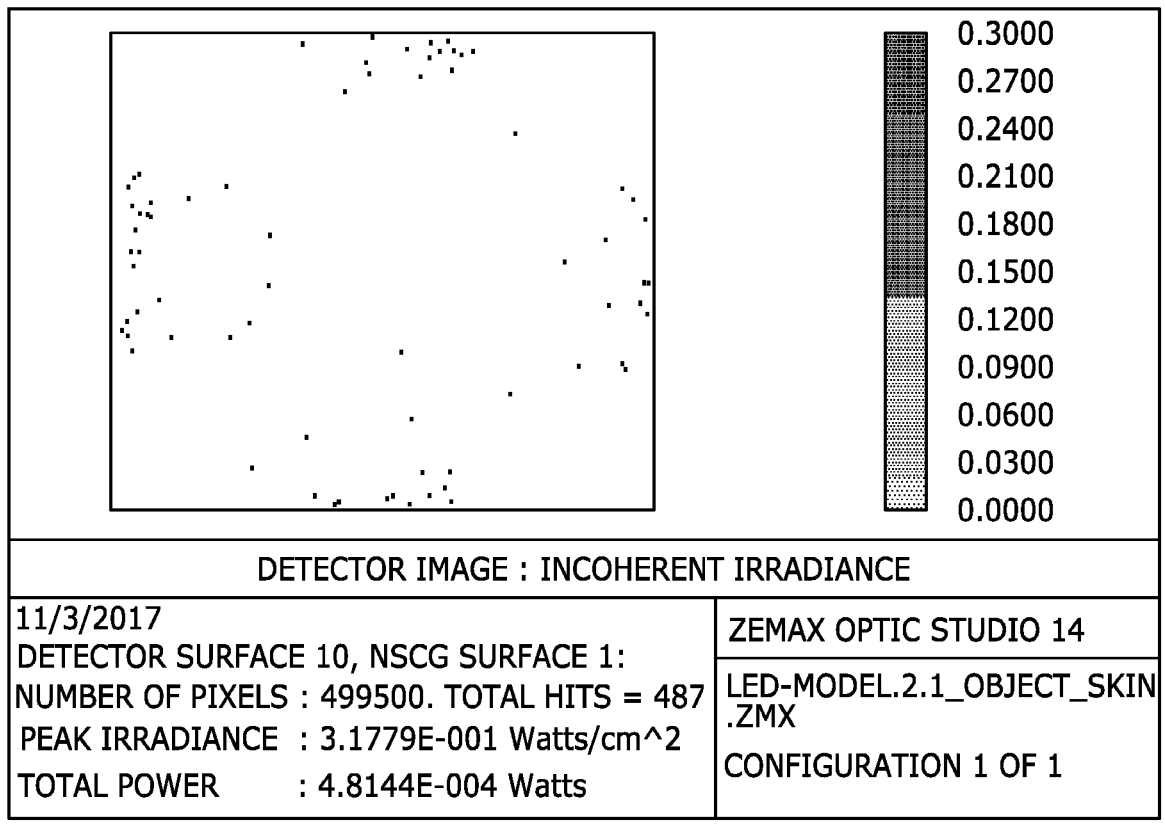
FIG. 6F depicts an optical profile and power reaching the camera using an 82° source cone angle in accordance with an illustrative embodiment.

FIGS. 6A-6F depict an optical profile and power reaching the camera from the diffusive sample for various source cone angles. Specifically, FIG. 6A depicts an optical profile and power reaching the camera using a 50° source cone angle in accordance with an illustrative embodiment. FIG. 6B depicts an optical profile and power reaching the camera using a 60° source cone angle in accordance with an illustrative embodiment. FIG. 6C depicts an optical profile and power reaching the camera using a 70° source cone angle in accordance with an illustrative embodiment. FIG. 6D depicts an optical profile and power reaching the camera using a 75° source cone angle in accordance with an illustrative embodiment. FIG. 6E depicts an optical profile and power reaching the camera using a 80° source cone angle in accordance with an illustrative embodiment. FIG. 6F depicts an optical profile and power reaching the camera using an 82° source cone angle in accordance with an illustrative embodiment. With respect to the results using an 80° source cone angle in FIG. 6E, it can be seen that the optical power reaching the camera is maximized as compared to the other source cone angles.

Figure 7A:
FIG. 7A depicts a test image captured by an infrared camera of a test surface that is tilted 10° relative to an 80° source cone in accordance with an illustrative embodiment.
Figure 7B:
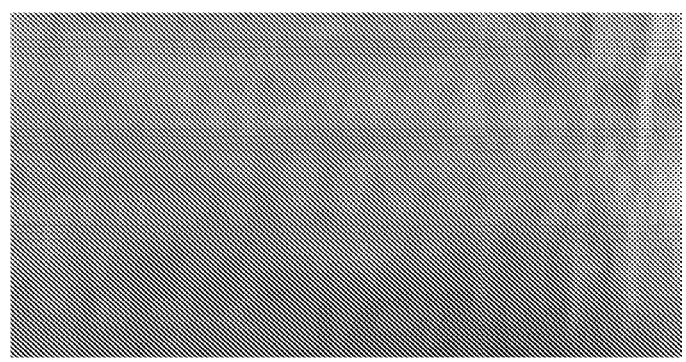
FIG. 7B depicts a test image captured by an infrared camera of a test surface that is normal to an 80° source cone in accordance with an illustrative embodiment.

In addition to simulations, an actual source cone having an 80° angle was constructed and tested using four red LEDs symmetrically positioned on the vertices of a rectangle at the base of the source cone. The system was then tested on a rough and reflective surface by placing the source cone normal to the surface and tilted at 10 degrees relative to the surface. As expected based on the simulations, there was a significant reduction in specular reflection when the sample surface is orthogonal to the cone as opposed to when there is a 10 degree tilt between the cone and the sample surface. FIG. 7A depicts a test image captured by an infrared camera of a test surface that is tilted 10° relative to an 80° source cone in accordance with an illustrative embodiment. FIG. 7B depicts a test image captured by an infrared camera of a test surface that is normal to an 80° source cone in accordance with an illustrative embodiment. It can be seen that the image of FIG. 7B, in which the test surface is orthogonal to the source cone, has significantly less specular reflection than the image of FIG. 7A.

Figure 8A:
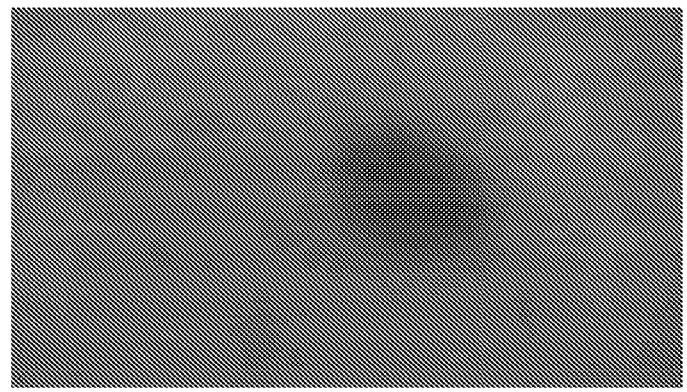
FIG. 8A depicts a mole imaged at 460 nm using a multispectral imaging system in accordance with an illustrative embodiment.
Figure 8B:
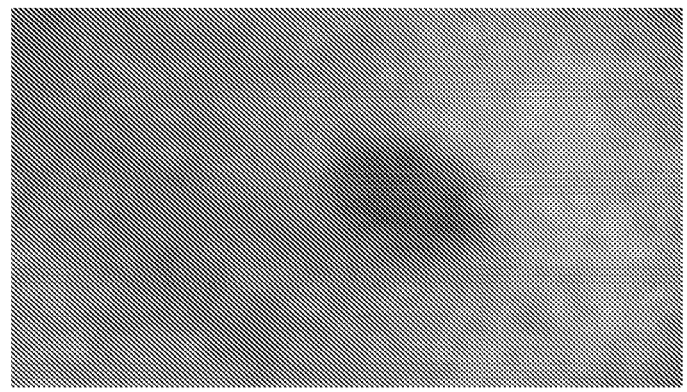
FIG. 8B depicts the mole imaged at 515 nm using the multispectral imaging system in accordance with an illustrative embodiment.
Figure 8C:
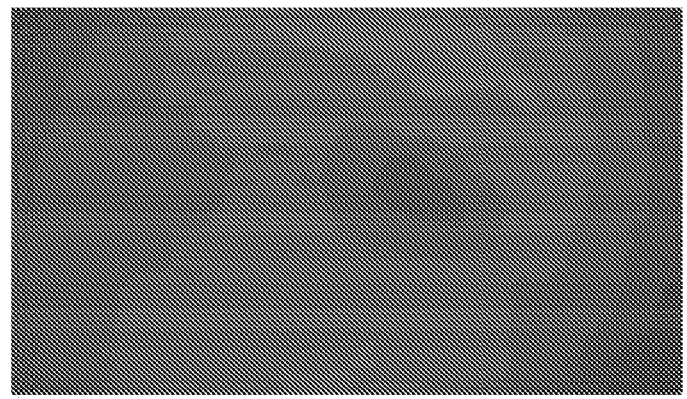
FIG. 8C depicts the mole imaged at 645 nm using the multispectral imaging system in accordance with an illustrative embodiment.
Figure 8D:
FIG. 8D depicts the mole imaged at 1450 nm using the multispectral imaging system in accordance with an illustrative embodiment.
Figure 8E:
FIG. 8E depicts the mole imaged at 1600 nm using the multispectral imaging system in accordance with an illustrative embodiment.

A prototype of the system was also used to image a mole at 5 different illumination wavelengths (460 nm, 515 nm, 645 nm, 1450 nm, and 1600 nm). FIG. 8A depicts a mole imaged at 460 nm using a multispectral imaging system in accordance with an illustrative embodiment. FIG. 8B depicts the mole imaged at 515 nm using the multispectral imaging system in accordance with an illustrative embodiment. FIG. 8C depicts the mole imaged at 645 nm using the multispectral imaging system in accordance with an illustrative embodiment. FIG. 8D depicts the mole imaged at 1450 nm using the multispectral imaging system in accordance with an illustrative embodiment. FIG. 8E depicts the mole imaged at 1600 nm using the multispectral imaging system in accordance with an illustrative embodiment. It is apparent from FIGS. 8D and 8E that the mole is not distinguishable from the surrounding tissue at 1450 nm or at 1600 nm. The reason for this is that melanin does not absorb the wavelengths of 1450 nm or 1600 nm. Such information can be very helpful in detecting skin tumors and determining their type.

Figure 9:
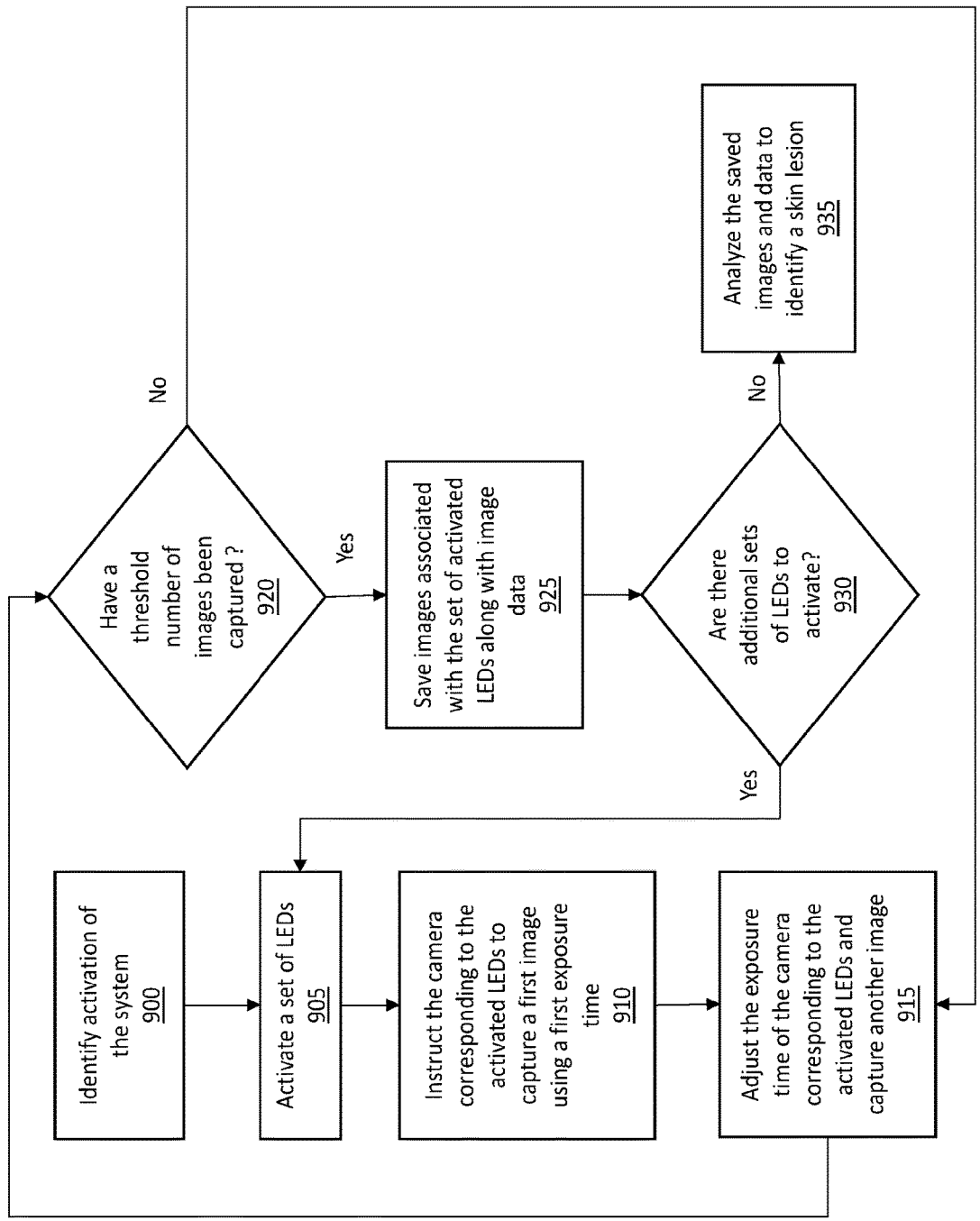
FIG. 9 is a flow diagram depicting operations performed by a multispectral imaging system in accordance with an illustrative embodiment.

FIG. 9 is a flow diagram depicting operations performed by a multispectral imaging system in accordance with an illustrative embodiment. In alternative embodiments, fewer, additional, and/or different operations may be performed. Additionally, the use of a flow diagram is not meant to be limiting with respect to the order of operations performed. The multispectral imaging system described with respect to FIG. 9 can include any of the features described herein. In an illustrative embodiment, the multispectral imaging system is positioned such that the source cone is orthogonal to a tissue sample. In an operation 900, an activation of the system is identified. The activation can be performed by a user to commence image generation, and can be identified by a processor (or microcontroller) of the imaging system. In one embodiment, the system can be activated using a mechanical trigger such as the trigger switch 120 depicted in FIG. 1. Alternatively, the system can be activated responsive to an electronic instruction received from a user device that is in communication with the system.

In an operation 905, the system activates a set of LEDs. In an illustrative embodiment, the system can include six sets of LEDs operating at different wavelengths and each set of LEDs can include four LEDs of a given wavelength. In one embodiment, the system can be programmed to cycle through the sets of LEDs in a predetermined order. Alternatively, a user can specify the order in which the LEDs are to be activated. In another alternative embodiment, multiple sets of LEDs can be simultaneously activated. In an operation 910, the system instructs the camera corresponding to the activated set of LEDs to capture a first image using a first exposure time. For example, if the activated set of LEDs falls within the visible light range, the system can activate the visible light camera to capture the image. Similarly, if the activated set of LEDS falls within the SWIR range, the infrared camera can be used to capture the image. The first exposure time can be set based on the camera being used, the wavelength being used, the skin tone of the sample being imaged, ambient light conditions, etc.

In an operation 915, the system adjusts the exposure time of the camera corresponding to the activated LEDs and captures another image. In an operation 920, the system determines whether a threshold number of images has been captured using the activated set of LEDs. In an illustrative embodiment, the threshold number of images can be 10 such that the system captures 10 images of a given wavelength using a different exposure time for each image. In alternative embodiments, the threshold number of images can be 2, 4, 6, 8, 12, etc. The reason for capturing multiple images using different exposure times is to mitigate the issue of image saturation, which can occur due to variations in reflectivity of different lesions on different patients. If the system determines that the threshold number of images has not been captured, the system again adjusts the exposure time of the camera corresponding to the activated LEDs and captures another image in the operation 915. In an alternative embodiment, a single image may be captured using each set of LEDs.

If the system determines that the threshold number of images has been captured, the system saves the images associated with the set of activated LEDs along with image data in an operation 925. In an illustrative embodiment, the images can be saved in a folder with a predefined name and directory path. In another illustrative embodiment, each set of images of a particular wavelength is stored in its own sub-folder. The image data saved along with each image can include the exposure time for the image, the LED wavelength used, the illumination power, a timestamp, and/or any additional information. The images can be saved locally on a system memory. Additionally or alternatively, the images may be transferred via a wired or wireless communication connection to another computing device such as a laptop, smart phone, server, etc.

In an operation 930, the system determines whether there are any additional sets of LEDs to activate. As an example, the system may include 6 sets of LEDs, and may sequentially activate all 6 sets. Alternatively, in some embodiments and/or specific applications, the system may be configured to only activate a subset of LED sets (e.g., 4 LED sets). In another alternative embodiment, one or more sets of LEDs may be simultaneously activated. If it is determined in the operation 930 that there are additional sets of LEDs to activate, the system continues to conduct operations 905-925, as discussed above. In an illustrative embodiment, the system uses independent LED sets as discussed above, and does not include a mechanical filter that is commonly used in existing imaging systems. Illuminating one or more single wavelengths at a time without the use of a filter allows for rapid switching of wavelengths, which improves the overall speed of the system.

If the system determines that there are no additional sets of LEDs to activate, the saved images and data are analyzed to identify a skin lesion in an operation 935. In one embodiment, the images and data can be analyzed by the processor or microcontroller of the system. Alternatively, the images and data can be analyzed by a remote computing device that receives the images and data from the system. Any techniques known in the art of image analysis may be used to analyze the images and make determinations regarding skin lesions present in the images.

It is to be understood that any of the operations/processes described herein may be performed at least in part by a computing system that includes a processor, memory, transceiver, user interface, etc. The described operations/processes can be implemented as computer-readable instructions stored on a computer-readable medium such as the computer system memory. Upon execution by the processor, the computer-readable instructions cause the computing system to perform the operations/processes described herein.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A multispectral imaging apparatus, comprising:
   a processor;
   a plurality of sets of light-emitting diodes (LEDs) in communication with the processor, wherein one or more first sets of LEDs includes a wavelength in a visible range, and wherein one or more second sets of LEDs includes a wavelength in a short wavelength infrared range (SWIR);
   a truncated source cone through which light from the plurality of sets of LEDs is directed onto a surface and through which light reflected off of the surface is received, wherein the truncated source cone has a source cone angle that is determined based on a ray tracing simulation, and wherein the source cone angle comprises an angle formed between a base of the truncated source cone and a sidewall of the truncated source cone;
   a visible light camera in communication with the processor and configured to capture a plurality of first images of the surface based on reflected light that originates from the one or more first sets of LEDS with the wavelength in the visible range, wherein each of the plurality of first images is captured using a distinct visible light exposure time; and
   an infrared light camera in communication with the processor and configured to capture a plurality of second images of the surface based on reflected light that originates from the one or more second sets of LEDs with the wavelength in the SWIR, wherein each of the plurality of second images is captured using a distinct infrared light exposure time.

2. The apparatus of claim 1, further comprising a lens tube positioned to receive the reflected light that originates from the one or more first sets of LEDs and the reflected light that originates from the one or more second sets of LEDs by way of the truncated source cone, wherein the lens tube includes a first lens and a second lens.

3. The apparatus of claim 2, wherein the first lens and the second lens are identical.

4. The apparatus of claim 2, further comprising a beam splitter configured to direct the reflected light that originates from the one or more first sets of LEDs to the visible light camera and to direct the reflected light that originates from the one or more second sets of LEDs to the infrared light camera.

5. The apparatus of claim 4, further comprising a visible light tube positioned between the beam splitter and the visible light camera, wherein the visible light tube is configured to receive the reflected light that originates from the one or more first sets of LEDs and direct the reflected light to the visible light camera.

6. The apparatus of claim 4, further comprising an infrared light tube positioned between the beam splitter and the infrared light camera, wherein the infrared light tube is configured to receive the reflected light that originates from the one or more second sets of LEDs and direct the reflected light to the infrared light camera.

7. The apparatus of claim 1, further comprising a trigger switch configured to activate the multispectral imaging apparatus.

8. The apparatus of claim 1, further comprising a handle that allows a user to position the multispectral imaging apparatus, wherein the multispectral imaging apparatus is portable.

9. The apparatus of claim 1, further comprising an electronics case positioned adjacent to the truncated source cone, wherein the electronics case houses the processor and a printed circuit board that includes at least a memory.

10. The apparatus of claim 1, wherein the truncated source cone includes a cone angle of 80 degrees.

11. The apparatus of claim 1, wherein the plurality of sets of LEDs comprises 6 sets of LEDs, and wherein each set of LEDs includes a distinct wavelength.

12. The apparatus of claim 11, wherein the 6 sets of LEDs include a first set of LEDs at 460 nanometers (nm), a second set of LEDs at 515 nm, a third set of LEDs at 645 nm, a fourth set of LEDs at 940 nm, a fifth set of LEDs at 1450 nm, and a sixth set of LEDs at 1600 nm.

13. The apparatus of claim 1, wherein each of the plurality of sets of LEDs includes 4 LEDs of identical wavelength.

14. The apparatus of claim 13, wherein the 4 LEDs in each of the plurality of sets of LEDs is symmetrically positioned around a base of the truncated source cone.

* * * * *